United States Patent
Knapp

[19]

[11] Patent Number: 5,940,176
[45] Date of Patent: Aug. 17, 1999

[54] ACCURATE MANUAL ILLUMINATION INSPECTION

[76] Inventor: Julius Z. Knapp, 22 Foxwood Dr., Somerset, N.J. 08873

[21] Appl. No.: 08/714,232

[22] Filed: Sep. 16, 1996

[51] Int. Cl.⁶ .................................................. G01N 21/00
[52] U.S. Cl. ............................................. 356/240
[58] Field of Search .................................. 356/427, 240; 362/32, 125, 249

[56] References Cited

U.S. PATENT DOCUMENTS

| | | | |
|---|---|---|---|
| 3,914,058 | 10/1975 | Knapp et al. | 356/427 |
| 4,209,802 | 6/1980 | Fogg et al. | 356/427 |
| 5,180,222 | 1/1993 | Robinson | 362/125 |

*Primary Examiner*—Richard A. Rosenberger
*Attorney, Agent, or Firm*—Graham & James LLP

[57] ABSTRACT

A method and device for the accurate manual inspection of three-dimensional (not flat) samples, such as pharmaceutically injectable vials, for particle contamination, which samples are illuminated with diffused (non-point) light. Opposing vertically positioned and spaced illumination sources are provided above and below the vial, with the vial being positioned in an inspection volume at the illumination midpoint (lumen light balance) between the illumination sources. The illumination midpoint, for light sources of equal intensity, is also the physical midpoint therebetween. Though the mid-point is not the position of maximum illumination for light sources, normal variation in manual inspections, e.g., variations in inspector height and deviations caused by manual handling of the vial, at the mid-point, result in minimal deviations in illumination, with resulting greater accuracy and replicability of inspection results. The station further optionally includes a light-dark-light changeable background for inspection of different contrast particles which may be in the vial, without removal of the vial from the inspection point at the illumination midpoint.

20 Claims, 6 Drawing Sheets

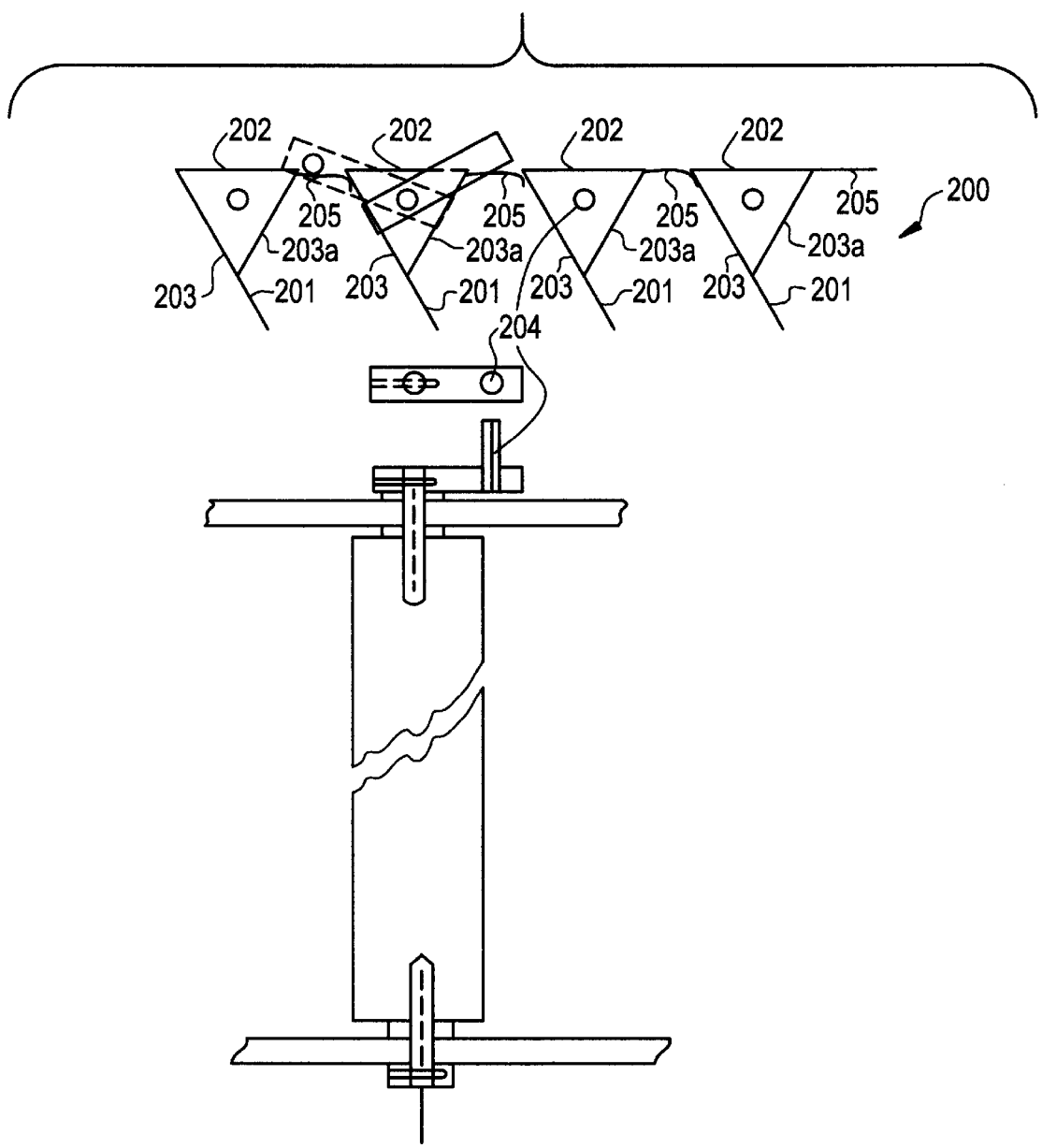

ACCURATE MANUAL ILLUMINATION INSPECTION

FIELD OF THE INVENTION

This invention relates to the inspection of uniformly illuminated three dimensional objects, and particularly to manual inspection of transparent vials, containing pharmaceutical injectables, for particle contamination.

BACKGROUND OF THE INVENTION

The present manual inspection methodology for inspection of vials, containing pharmaceutical injectables, for particle contamination, involves a two step particle inspection sequence. The first step is the inspection of the container for black or dark particles in front of a flat white background which is used to optimize the contrast of black particles. The second inspection step occurs in front of a flat black background to improve the contrast and thus the detection for white particles. In both cases, the container is manipulated to induce motion in any suspended particles to permit the human eye to distinguish between stationary container defects and moving contaminating particles. In present practice, the container is moved about 8 to 12 inches between the white and black background inspection locations. Repositioning the inspected container requires both refocusing of the eyes and accurate repositioning of the inspector's head and the inspected container for each part of the inspection since the container is inspected at a near focus position, approximately 10 inches from the eye. These wasted motions reduce the rate at which an inspection of acceptable quality can be achieved. The energy lost in these non-productive motions result in deteriorated inspection performance due to the cumulative effect of inspector fatigue and can reduce inspector efficiency by as much as 30% at the end of a full work day, especially when a magnifying lens is used in the inspection. Repositioning can also vary the illumination available for inspection of the container, thereby introducing additional variability in the results of the inspection.

A light inspection booth used in the present manual inspection procedures for contaminating particles in pharmaceutical products, comprises of a 60 Hz ballast which excites a pair of 20 watt 1½ inch diameter daylight fluorescent lamps. The fluorescent lamps are arranged in an open lighting fixture and are mounted 20 inches above (lateral positioning results in unwanted glare on the inspected container) the work surface. The booth can be used with or without a magnifying lens, which extends the visible range of the examined particles. Current illuminance recommendations for the aforementioned manual type of inspection recommend a minimum of 500 to a maximum of 1000 foot-candles, with a numerical mid-point value for the range being 750 foot-candles.

The inspection for contaminating particles in injectable solutions has been shown to be probabilistic in nature, and with inspection performed with a fluorescent light source, a rough relationship between the probability of detecting a particle in a container and the particle size has been established.

In the standardized inspection conditions employed (without a magnifying lens), a 50 $\mu$m particle was not detected, a 100 $\mu$m particle was detected 70% of the time and a 200 $\mu$m particle was consistently detected 100% of the time. As the light intensity employed for the inspection is increased or the contrast of the particle increases, the detection probability is increased, with the corollary being that reduced light intensity and contrast results in decreased detection probability.

The target of the manual inspection therefore is the visible particle size range greater than 100 $\mu$m. The experimental rejection probability for all particles in this size range evaluates the effectiveness of the manual inspection. Extensive biophysics literature on human vision has established that the light intensity used for the inspection and the contrast of the target against the background determine both the rate and the accuracy with which a critical inspection can be successfully accomplished. Conversely, the wider the latitude of the illuminance employed for the inspection, the more variable will be the results of a manual inspection. With uncontrolled luminance variation the position of the inspected container with respect to the light source can multiply the difficulty of obtaining a secure inspection for contaminating particles.

With present light sources, the light intensity at the inspection point varies with the size of the inspected container and its position with respect to the light source. These factors modify the illuminance available for inspection of contaminating particles and thus the security with which these particles are detected.

Current inspection booths have recently been modernized by replacing the two 20 watt lamps with a single 40 Watt 16 mm diameter hairpin lamp (e.g., G.E. F40/30BX/SPX/41RS or its Phillips equivalent PL-L 40W/30RS/41) in an open reflector. The variation of light intensity as a function of distance from the fluorescent lamp surface is overtly non-linear, which factor results in loss of detection security with extensive variations between similarly effected inspections.

Modernization with attempts to upgrade inspection reliability has generally focussed on enhancement of the degree of illumination and a flicker free source. No consideration has however been given to inspection condition variability which is the subject of the present invention.

An inspector's physical characteristics can have a profound effect on the results of a manual inspection. Thus, with an inspection position used by inspectors of standing heights ranging from 5' to 5'10", the variation in the inspection point for these inspectors, operating without a magnifying lens to define the inspection point, has been found to vary by as much as 8 inches. This 8 inch change in the position of the inspection point (relative to a stationary illumination source), results in a change in illuminance, at the spaced inspection points, for the inspection of the same container, by inspectors of different heights, of 652% (as shown from the ±4" range around the 8" illumination inspection distance of Table 1). The changing light intensity associated with the change in inspection position, especially of the magnitude described, contributes significantly to the variability of manual inspection results for the detection of particle contamination.

TABLE 1

| DISTANCE FROM LAMP SURFACE INCHES | RELATIVE DISTANCE $R_4/R$ | RELATIVE ILLUMINANCE $I/I_4$ |
|---|---|---|
| 4 | 1.00 | 1.0000 |
| 5 | 0.800 | 0.6833 |
| 6 | 0.666 | 0.3064 |
| 8 | 0.500 | 0.2093 |
| 10 | 0.400 | 0.1778 |
| 12 | 0.333 | 0.1533 |
| 14 | 0.286 | 0.1178 |

TABLE 1-continued

| DISTANCE FROM LAMP SURFACE INCHES | RELATIVE DISTANCE $R_4/R$ | RELATIVE ILLUMINANCE $I/I_4$ |
|---|---|---|
| 15 | 0.266 | 0.1047 |
| 16 | 0.250 | 0.0938 |
| 18 | 0.222 | 0.0767 |
| 20 | 0.200 | 0.0642 |

Variation of light intensity with distance from an open luminaire equipped with two 16 mm 40 watt fluorescent lamps normalized to the light intensity 4 inches from the source. A change of ± 4 inches of the inspection point from the location 8 inches below the lamp surface changes the illuminance 652%.

To reduce the variability of human inspection results for contaminating particles in injectable fluids (or for that matter any type of similar illuminated inspection such as inspection for checking weld integrity and the like), the conditions under which the inspection is conducted must be defined and accurately controlled or contained.

It is therefore an object of the present invention to provide a method, and arrangement for effecting the method, whereby variability of manual inspection results are minimized for an inspection volume.

It is a further object of the present invention to reduce such variability with respect to pharmaceutical injectables.

It is yet another object of the present invention to provide an inspection station with means for quickly varying the background to white and black (for appropriate light and dark particle inspection respectively) to obviate the necessity for excessive movement of the object to be inspected to further reduce variability and inspector fatigue.

These and other objects, features and advantages of the present invention will become more evident from the following discussion.

SUMMARY OF THE INVENTION

Generally the present invention comprises a method and device for the accurate (with minimal variability) manual inspection of extended two dimensional surfaces or three-dimensional (not flat) samples, such as pharmaceutically injectable vials, for particle contamination, which samples are illuminated with diffused (non-point) light. Opposing vertically positioned and spaced illumination sources are provided above and below the sample, such as a vial, with the inspection volume (volume of the object, and movement space as may be required for inspection) being positioned at and around the illumination midpoint (lumen light balance) between the illumination sources for minimal illumination variability as a function of distance from the illumination midpoint. The position of the illumination mid-point for the inspection volume is adjustable according to the eye level of the particular inspector, whereby the illumination midpoint is brought into alignment with such eye level. Since the illumination midpoint, for light sources of equal intensity, is also the physical midpoint therebetween, adjustment is readily physically effected. The adaptation of existing manual stations with lighting below the inspection volume is not to be construed as limiting. Thus, lighting at any point and angle relative to the inspection volume (and in a plane parallel to the inspector) is possible, as long as the lighting is symmetrically balanced to provide the requisite illumination mid-point, with the ultimate illuminated inspection station comprising a balanced series of lights positioned in a circle about the inspection volume. Similarly though the present invention is illustrated with respect to manual inspections, equivalent machine inspections which are dependent on minimized illumination variations are similarly within the purview of the present invention.

Though the mid-point is not the location of maximum illumination for the light sources employed, normal variation in manual inspections, e.g., variations in inspector height and deviations caused by manual handling of the vial, at the mid-point, result in minimal deviations in illumination, with resulting greater accuracy and replicability of inspection results. The mid-point illumination should however be of adequate recommended inspection intensity since it is normally the point of least illumination intensity. Accordingly the multiple light sources should be preselected to provide recommended illumination levels at the inspection midpoints.

In order to further enhance inspection security and to reduce inspector fatigue, it is preferred that there be no movement away from the designated inspection volume during any part of the inspection. Accordingly, it is preferred that the inspection be effected in front of a background which is automatically and quickly variable between light and dark to permit for optimal contrast for inspection for light and dark particles. The inspection station of the present invention therefore preferably further comprises means for varying the inspection background between light and dark while the vial is at the inspection point within the inspection volume.

In order to demonstrate the structure and effects of the present invention, the following drawings illustrate and serve to compare the prior art and the present invention with experimentally set forth parameters and results:

SHORT DESCRIPTION OF THE DRAWINGS

FIG. 6 is a top section view of a changeable white-black background surface for the inspection station of FIG. 5.

DETAILED DESCRIPTION OF THE INVENTION AND THE DRAWINGS

Figure 1:
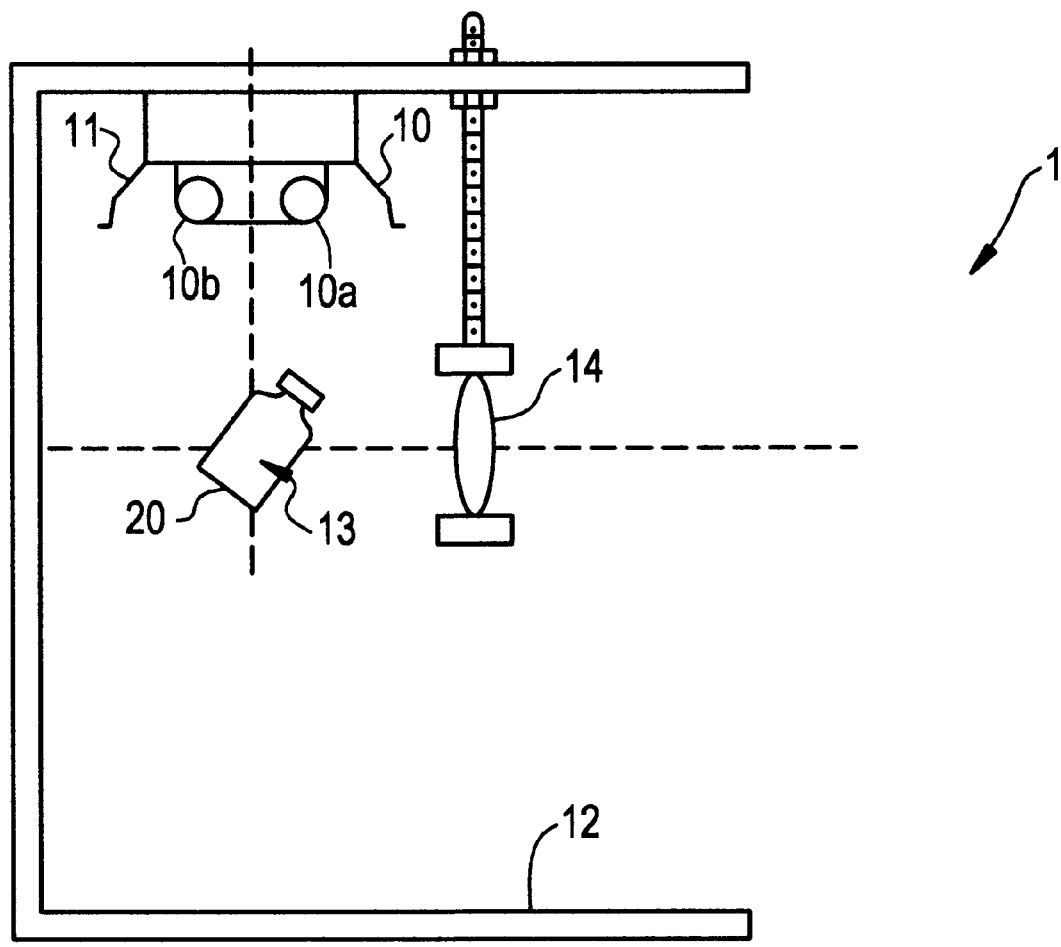
FIG. 1 is a schematic rendering of a prior art inspection work station.

A prior art light inspection booth or station 1 used in the prior art manual inspection procedures, for detection of contaminating particles in pharmaceutical products, typically has a single light source 10. The light source consists of a 60 Hz. ballast that excites a pair of 20 watt 1½ inch diameter daylight fluorescent lamps, 10a and 10b. The fluorescent lamps are positioned in an open lighting fixture 11 which is mounted 20 inches above the work surface 12 and about 8 inches from the inspection point 13. The booth can be used with or without a magnifying lens 14. The lamp wattage, the distance from the lamps to the inspected container 20, and the 225 foot-candle illuminance produced by this light source for the inspection are based on the Illumination Engineering Society recommendations.

Figure 5:
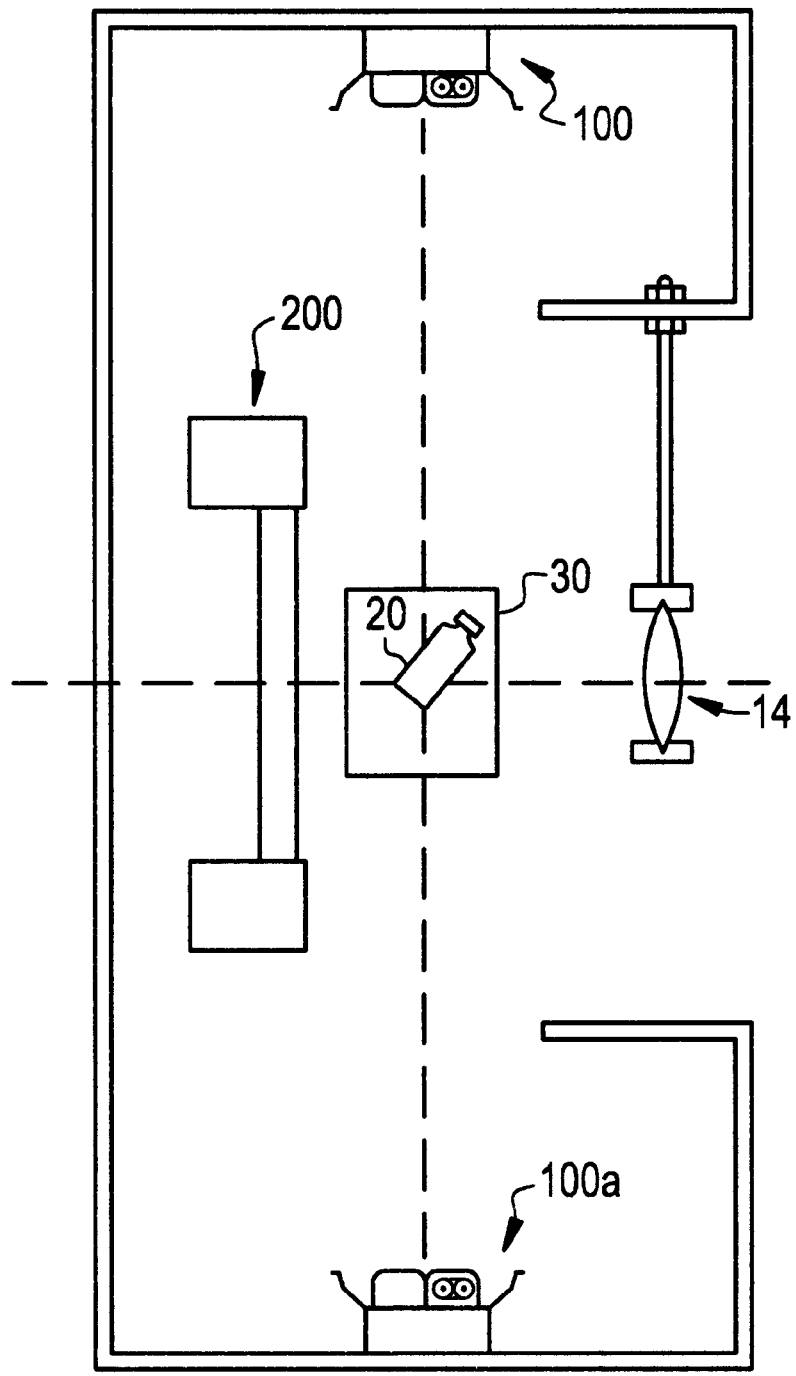
FIG. 5 is a schematic rendering of the inspection station of the present invention.

In consideration of the present invention it is noted that movement away from a light source 10 reduces the light intensity received from that source. However, in accordance with the present invention, and as shown in FIG. 5, a compensation mechanism to maintain constant light intensity can be realized when two light sources 100 and 100a are arranged in a line pair and directed toward each other. Any such combination results in less variation of lighting intensity in the inspection volume than the single light source, which is in present use.

Accurate control of inspection light intensity for the use in the inspection or measurement of flat objects, or for the measurement of dimensions that are measured in a single plane, is readily effected. The object to be examined is simply inspected at a specified distance in front of a uniformly lighted panel.

However, accurate inspections for particulate contamination of the contents of transparent containers 20 filled with injectable pharmaceutical products require the use of a uniformly lighted volume (inspection volume) 30 rather than a single plane. The volume requirements are based on the physical size of the container plus the volume required to enclose the space in which container movement is effected, to impart motion to the suspended particles. Particle motion is required to provide the inspector with a means to differentiate contaminating particles within the liquid from optical container flaws and surface dirt on the container. The maintenance of accurate light intensity is also important in the high speed automated inspection of three dimensional objects.

The ideal light source for development of a volume of constant illumination is a light source with a linear variation of light intensity at a distance from the source. With such an ideal source available, a constant illumination volume can be realized between a line-pair of such light sources. The line-pair arrangement consists of a pair of parallel, inward facing lamps mounted as if on opposite equal faces of a rectangular parallelepiped corresponding to the size of the lamps in their fixture. On the line between the equal light sources, movement away from one source, with its attendant loss of light intensity, is completely compensated by the increased intensity available from the corresponding movement to the second light source of the pair. Thus, with constantly maintained illumination between the light sources at all points between the light sources, movement in an inspection volume provides neither variation in illumination nor any variation in inspection security.

However, the variation of light intensity from a practical light source is not linear with distance. All real or practical light sources (e.g. lights 100 and 100a in FIG. 5) have a non linear relationship between their delivered light intensity and the distance from the light source. With these light sources, there is no distance from a single light source around which an even, symmetrical function of light intensity, $f(x)=f(-x)$ and distance can be developed since these practical light sources are odd functions of light intensity and distance.

Optimum symmetry with practical light sources (e.g., a flourescent light source as in the prior art) is at the mid-point 50 between the light sources where the light delivered from each source is equal. However, at this mid point, the total illumination is at a minimum and any departure from this equidistant point between the light sources actually increases the inspection point illumination.

TABLE 2

| DISTANCE FROM LAMP 1 SURFACE INCHES | RELATIVE DISTANCE | RELATIVE ILLUMINANCE LAMP 1 | RELATIVE ILLUMINANCE LAMP 2 | RELATIVE TOTAL ILLUMINANCE |
|---|---|---|---|---|
| 4 | 1.000 | 1.0000 | 0.0625 | 1.0625 |
| 5 | 0.800 | 0.6400 | 0.0711 | 0.7111 |
| 6 | 0.666 | 0.4444 | 0.0916 | 0.5360 |
| 7 | 0.571 | 0.3265 | 0.946 | 0.4211 |
| 8 | 0.500 | 0.2500 | 0.1111 | 0.3611 |
| 9 | 0.444 | 0.1975 | 0.1322 | 0.3297 |
| 10 | 0.400 | 0.1600 | 0.1600 | 0.3200 |
| 11 | 0.364 | 0.1322 | 0.1975 | 0.3297 |
| 12 | 0.333 | 0.1111 | 0.2500 | 0.3611 |
| 13 | 0.308 | 0.0946 | 0.3265 | 0.4211 |
| 14 | 0.286 | 0.0816 | 0.4444 | 0.5360 |
| 15 | 0.266 | 0.0711 | 0.6400 | 0.7111 |
| 16 | 0.250 | 0.0625 | 1.0000 | 1.0625 |
| 20 | 0.200 | 0.0040 | — | — |

Variation of light intensity on the axis between a line-pair of point sources normalized to the light intensity 4 inches from each source. The minimum total light intensity is at the midpoint between the two point sources. A change of ± 4 inches of the inspection point (from 4 inches to 12 inches) from the location 8 inches below the lamp surface used in the 1980 paper changes the illuminance 900%. A change of ± 4 inches of the inspection point around the center point of the lamps reduces this change to 167.5%, a 5.4 fold reduction in variability.

Figure 2:
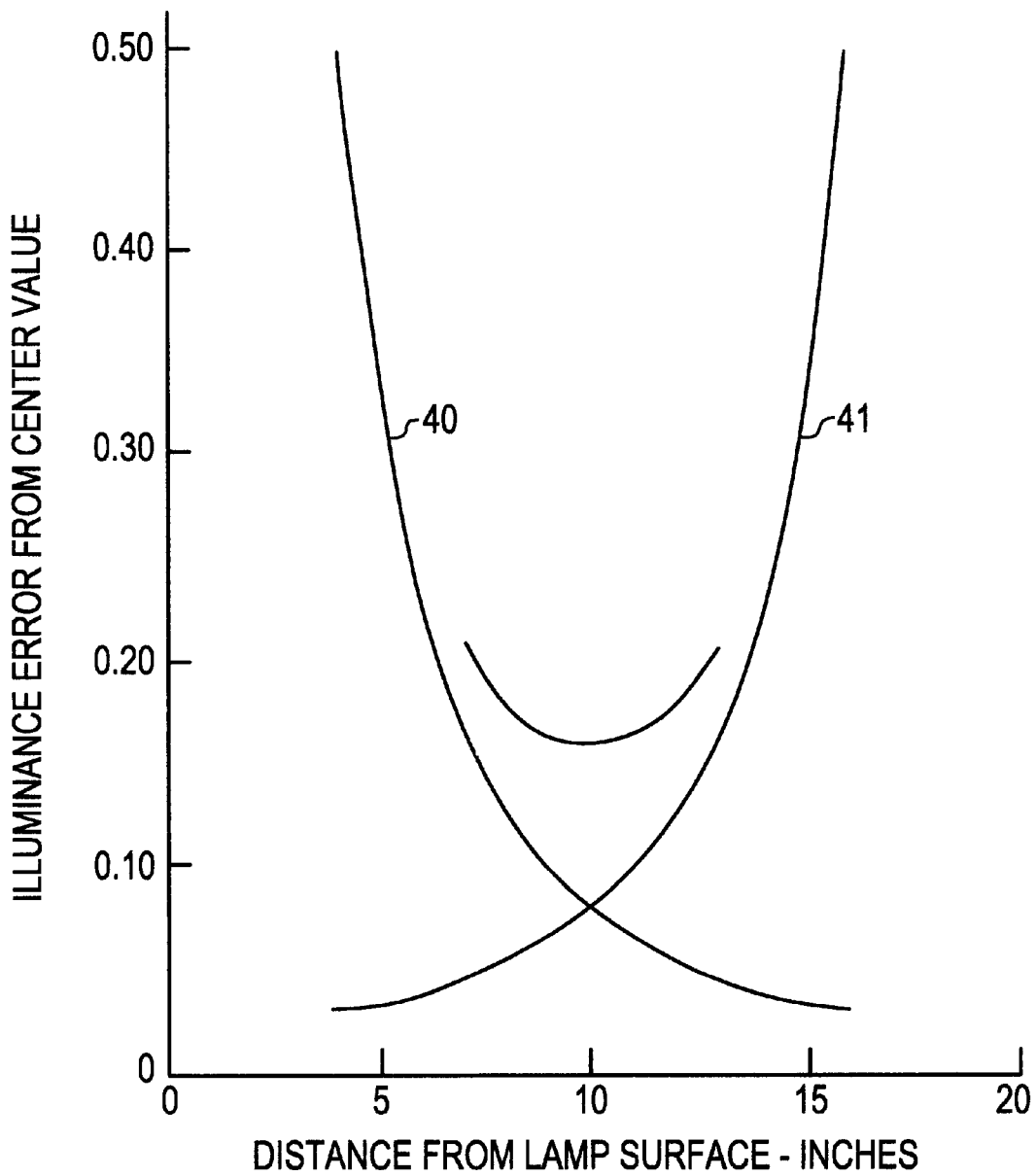
FIGS. 2–3 are variations of light intensity curves determined from lamp surface and center line respectively for point sources.
Figure 3:
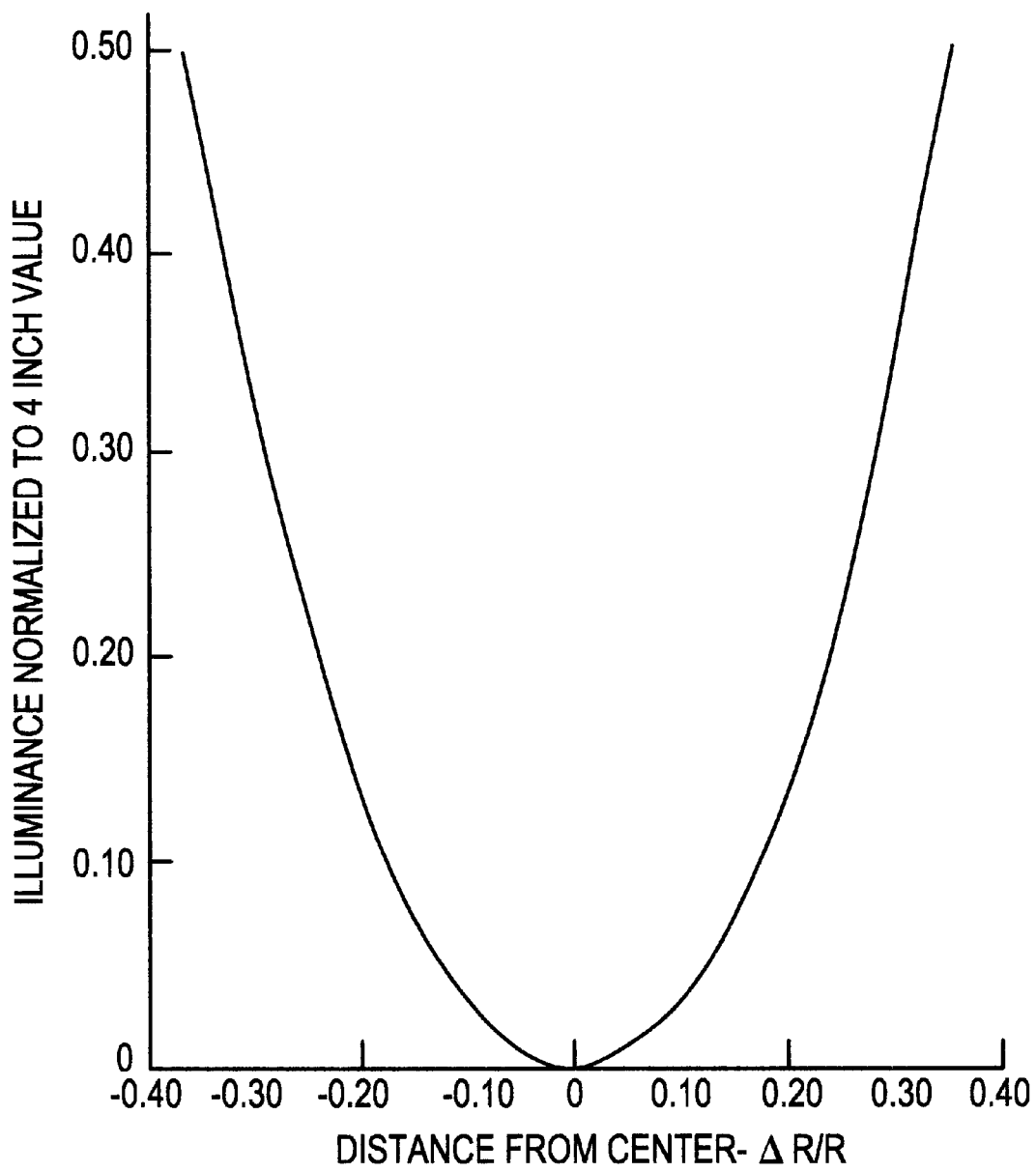

Table 2 illustrates this minimum of illumination at the equidistant point, in which a pair of point sources are separated vertically by 20 inches (the prior art illumination to work surface distance). The light intensity from lamp 1 at 4 inches is identical to the intensity of lamp 2 at 16 inches from lamp 1, etc. The total illuminance at points on the axis between the two point sources is the sum of the light delivered by each lamp. This total is shown in the column labeled "Relative Total Illuminance". This Table illustrates the achievement of an even, symmetrical function of light intensity versus distance between the two non-linear point sources. For better comparison to the experimental data of fluorescent lamps, the data of Table 2 is graphed in FIG. 2.

The left and right curves (40 and 41) show the contribution of each lamp to the inspection point illumination. The vertical axis represent fractions of the light intensity at 4 inches from the point source where the lamp intensities $I/I_0=1$. The horizontal axis is in inches and is the distance between the two point sources. The calculated data is shown for the distance from 4 inches from the top lamp to 4 inches from the bottom lamp. The greatest light linearized inspection volume is centered on the midpoint between the two sources. The minimum total illuminance is at the midpoint between the point sources. Any departure of the inspection point from the center reduces the light linearized volume obtainable from this arrangement.

The recent availability of improved fluorescent lamps that maintain their initial light intensity within 10% for 20,000 hours has made possible an improved, more accurate, inspection lighting method. These new 16 mm folded fluorescent lamps use improved, better balanced, 4100° Kelvin daylight phosphors (G.E. F40/30BX/SPX/41 RS or its Phillips equivalent PL-L 40W/30RS/41). Operated with high frequency electronic ballasts at 20 KHz they provide both flicker-free illumination and reduced light fixture heat. Both are important factors in minimization of inspector fatigue. The fluorescent lamps are hairpin shapes 16 mm in diameter lamps 22½ inches (527 mm) long. The 40 watt Phillips PL-L 40 w/30 RS with the 4100° K. color temperature or the G. E. equivalent are particularly suited for this type of inspection use. An open luminaire for two of these lamps mounted with all lamp tubes parallel to the backplane is equipped with 1½ inch wide by 2 inch high symmetrical channel reflectors on each side of the channel light fixture. To ensure freedom from end effect variation, the lighting zone used for inspection is limited to the central ⅔ of the lamps (approximately 14 inches). This provides a 12 inch deep×14 inch long constant intensity lighting zone area. The height of the inspection volume is determined by the distance from the lamp surface in which the magnitude and variability of the light intensity are determined to be within design limits.

A design for a constant light intensity volume that uses the illumination balance of the present invention, between an inward directed pair of lights must consider both the requirement for a constant intensity light source and the light source power required to deliver the specific level of light intensity required. The closer a selected operating mid-point is to the light source, the higher the light intensity and the steeper the variation of light intensity with distance from the source. The result of this relationship is that increasing the distance from the light sources to the center-point between the lights, increases the volume within which the light intensity is linearized. The increased volume within which lighting accuracy has been maintained is achieved at the price of a lower light intensity level. Accurate maintenance of the light intensity within a volume and the intensity of the illumination achieved are linked problems. The maintenance of light intensity and the delivery of a required level of light intensity is accomplished by increasing the available light source intensity and thus the power of the source.

The dimensions of the inspection volume for the inspection of injectable pharmaceutical products is related to the size of the containers to be inspected for contaminating particles. The height range of the inspected container for Small Volume Injectables, those with injectable volumes below 100 ml, varies from approximately 1½ to 4½ inches to as much as 9 inches for Large Volume Injectables. A 6 inch high inspection volume, in which light is accurately maintained, provides adequate volume for the particle contamination inspection of Small Volume Injectable containers up to 3 inches in height. The height of the inspection volume must include an allowance for the manual movements of the container during the inspection. A 9 inch high inspection volume should be adequate to inspect the full range of Small Volume Injectable containers (containers with volumes up to 100 ml and up to 4½ inches in height). A similar height margin for the inspection of Large Volume Injectables results in a 12 inch high inspection volume to accommodate the manual inspection movements of the larger container size (containers between 250 ml and 1 liter).

The following Examples are presented as being illustrative of determinations used in effecting the present invention in the inspection station shown in FIG. 5, with a pair of spaced 40 watt Phillips PL-L 40 w/30 RS lamps, in terms of lighting and distances for minimized variations in a determined inspection volume having at least minimum inspection illumination. Details contained therein are not to be construed as limitations on the present invention.

EXAMPLES 1–3

The use of experimental light intensity versus distance data for a specific lighting fixture guided by the design principles discussed above are applied to the realization of constant light inspection volumes at three lamp-to-lamp separation distances. The experimental data in Table 3 of light intensity versus distance data, in the form of the light delivered by each lamp is mapped in adjacent columns for the lamp to lamp separation distance selected, with $I_0$ being the reference light intensity at the reference position $R_0$. The sum of the light from both sources at each point is the total light delivered to that point in the space between the two lamps.

TABLE 3

BALANCED POINT SOURCES

| ±ΔR/R$_0$ | I/I$_0$ | PERCENT INCREASE | REMARKS |
| --- | --- | --- | --- |
| 0.00 | 1.0000 | 0.00 | Center point illumination reference level at ΔR/R$_0$ = 0 |
| 0.05 | 1.0075 | 0.75 | |
| 0.083 | 1.021 | 2.10 | |
| 0.10 | 1.031 | 3.1 | |
| 0.125 | 1.048 | 4.8 | |
| 0.15 | 1.070 | 7.0 | |
| 0.167 | 1.087 | 8.7 | |
| 0.178 | 1.100 | 10.0 | |
| 0.20 | 1.129 | 12.9 | |
| 0.25 | 1.209 | 20.9 | |
| 0.30 | I.316 | 31.6 | |
| 0.33 | 1.396 | 39.6 | |
| 0.35 | 1.458 | 45.8 | |
| 0.3625 | 1.500 | 50.0 | |
| 0.40 | 1.644 | 64.4 | |
| 0.50 | 2.222 | 122.2 | |
| 0.60 | 3.320 | 232.0 | |

Normalized variation of illuminance with distance between two equal point sources relative to the light intensity at 4 inches from the point light source. The total illuminance at any point between the two lights is the sum of the contribution from each lamp. Inspection of the summed light curve shows that a 10% I/I$_0$ limit is reached at ΔR/R$_0$ of 18%. The use of a line pair of light sources decreased the variability of illumination 90 fold.

Tables 4, 5 and 6 for lamp to lamp separation distances of 20, 40 and 60 inches respectively, demonstrate the procedure:

TABLE 4

| DISTANCE FROM UPPER LAMP SURFACE | ILLUMINANCE FOOT-CANDLES | | |
| --- | --- | --- | --- |
| INCHES | LAMP 1 | LAMP 2 | sum |
| 0 | — | — | — |
| 2 | — | — | — |
| 4 | 5500 | 516 | 6016 |
| 5 | 3758 | 576 | 4334 |
| 6 | 2753 | 648 | 3269 |
| 7 | 2116 | 745 | 2861 |
| 8 | 1685 | 843 | 2528 |
| 9 | 1378 | 978 | 2356 |
| 10 | 1151 | 1151 | 2306 |
| 11 | 978 | 1378 | 2356 |
| 12 | 843 | 1685 | 2528 |

TABLE 4-continued

| DISTANCE FROM UPPER LAMP SURFACE | ILLUMINANCE FOOT-CANDLES | | |
|---|---|---|---|
| INCHES | LAMP 1 | LAMP 2 | sum |
| 13 | 745 | 2116 | 2861 |
| 14 | 648 | 2753 | 3269 |
| 15 | 576 | 3758 | 4334 |
| 16 | 516 | 5500 | 6016 |
| 18 | — | — | — |
| 20 | — | — | — |

Variation of illumination with distance from the upper lamp source for an inspection operation using a balanced pair of fluorescent fixtures with 20 inches between the front surfaces of the two sets of lamps. The fixtures are equipped with two 16 mm diameter 40 watt fluorescent lamps (G.E. F40/30BX/SPX/41 RS or its Phillips equivalent PL-L 40W/30RS/41) mounted with all lamp tubes in parallel to the back plane on a white channel mounting with 1½ wide by 2 inch high symmetrical channel reflectors. The inspection point is at the midpoint between the two lamps and is adjusted to the inspector's eye level.

TABLE 5

| DISTANCE FROM UPPER LAMP SURFACE INCHES | ILLUMINANCE FOOT-CANDLES | | | |
|---|---|---|---|---|
| | LAMP 1 | LAMP 2 | sum | |
| 0 | — | — | — | |
| 2 | — | — | — | |
| 4 | 5500 | 129 | 5629 | |
| 6 | 2753 | 143 | 2896 | |
| 8 | 1685 | 158 | 1843 | |
| 10 | 1151 | 176 | 1327 | |
| 12 | 843 | 199 | 1042 | |
| 14 | 648 | 225 | 873 | |
| 16 | 516 | 258 | 774 | |
| 18 | 422 | 300 | 722 | |
| 20 | 353 | 353 | 706 | $I_{MIN}$ At midpoint between lamps. |
| 22 | 300 | 422 | 722 | |
| 24 | 258 | 516 | 774 | |
| 26 | 225 | 648 | 873 | |
| 28 | 199 | 843 | 1042 | |
| 30 | 176 | 1151 | 1327 | |
| 32 | 158 | 1685 | 1843 | |
| 34 | 143 | 2753 | 2896 | |
| 36 | 129 | 5500 | 5629 | |
| 38 | — | — | — | |
| 40 | — | — | — | |

Variation of illumination with distance from the upper lamp source for an inspection operation using a balanced pair of fluorescent fixtures with 40 inches between the front surfaces of the two sets of lamps. The fixtures are equipped with two 16 mm 40 watt fluorescent lamps (G.E. F40/30BX/SPX/41 RS or its Phillips equivalent PL-L 40W/30RS/41) mounted with all lamp tubes in parallel to the back plane on a white channel mounting with 1½ wide by 2 inch high symmetrical channel reflectors. The inspection point is at the midpoint between the two lamps and is adjusted to the inspector's eye level.

TABLE 6

| DISTANCE FROM UPPER LAMP SURFACE | ILLUMINANCE FOOT-CANDLES | | |
|---|---|---|---|
| INCHES | LAMP 1 | LAMP 2 | sum |
| 0 | — | — | — |
| 2 | — | — | — |
| 4 | 5500 | 61.0 | 5561 |
| 6 | 2753 | 64.9 | 2817.9 |
| 8 | 1685 | 69.2 | 1754.2 |
| 10 | 1151 | 74.0 | 1225 |
| 12 | 843 | 79.1 | 922.1 |

TABLE 6-continued

| DISTANCE FROM UPPER LAMP SURFACE | ILLUMINANCE FOOT-CANDLES | | |
|---|---|---|---|
| INCHES | LAMP 1 | LAMP 2 | sum |
| 14 | 648 | 85.1 | 733.1 |
| 16 | 516 | 91.8 | 607.8 |
| 18 | 422 | 99.4 | 521.4 |
| 20 | 353 | 108 | 461 |
| 22 | 300 | 118 | 418 |
| 24 | 258 | 129 | 387 |
| 26 | 225 | 143 | 368 |
| 28 | 199 | 158 | 357 |
| 30 | 176 | 176 | 352 |
| 32 | 158 | 199 | 357 |
| 34 | 143 | 225 | 368 |
| 36 | 129 | 258 | 387 |
| 38 | 118 | 300 | 418 |
| 40 | 108 | 353 | 461 |
| 42 | 99.4 | 422 | 521.4 |
| 44 | 91.8 | 516 | 607.8 |
| 46 | 85.1 | 648 | 733.1 |
| 48 | 79.1 | 843 | 922.1 |
| 50 | 74.0 | 1151 | 1225 |
| 52 | 69.2 | 1685 | 1754.2 |
| 54 | 64.9 | 2753 | 2817.9 |
| 56 | 61.0 | 5500 | 5561 |
| 58 | — | — | — |
| 60 | — | — | — |

Variation of illumination with distance from the upper lamp source for an inspection operation using a balanced pair of fluorescent fixtures with 60 inches between the front surfaces of the two sets of lamps. The fixtures are equipped with two 16 mm diameter 40 watt fluorescent lamps (G.E. F40/30BX/SPX/41R5 or its Phillips equivalent PL-L 40W/30RS/41) mounted with all lamp tubes in parallel to the back plane on a white channel mounting with 1½ wide by 2 inch high symmetrical channel reflectors. The inspection point is at the midpoint between the two lamps and is adjusted to the inspector's eye level.

For good comparability of the test data, all three tests are performed with the same lamp configuration. The test results are shown in FIG. 4, with curves 42, 43 and 44, corresponding to the three lamp separation distances of 20, 40 and 60 inches respectively.

Figure 4:
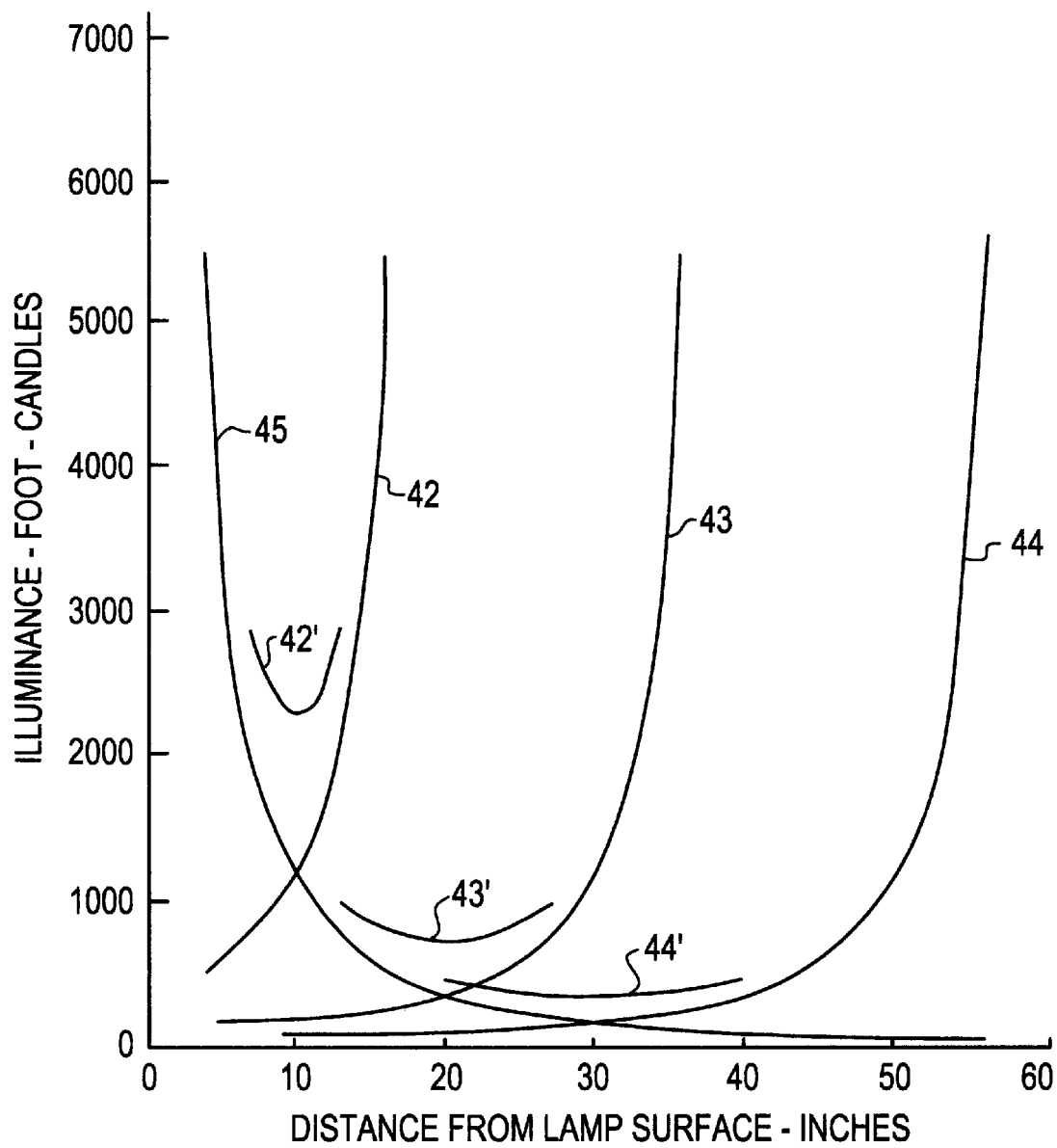
FIG. 4 shows curves for inspection point lighting at various distances.

The three sets of illuminance vs. distance in FIG. 4 share common characteristics: the line-pairs used are equal in power and thus light intensity. With the symmetry of this arrangement, the minimum light intensity for the line pair of lights is at the center point between them. To emphasize the effect of the lamp to lamp spacing on the size of the linearized light region the three curve sets shown are determined with a fixed upper lamp position (curve 45). Either direction of movement from the centerpoint results in an increase of illuminance and an increase in the variability of illuminance intensity available for the manual inspection process.

For movement from the center point that is large enough, the total illuminance available for inspection approaches that of the single light source. Any use of an inward directed lighting arrangement reduces the illuminance variability of a single lamp source for inspection. The greatest improvement results when equal intensity light sources are employed and the centerpoint of the inspection volume coincides with the point at which the light intensity from each source is equal i.e. at the midpoint between them. Any departure from symmetry reduces the illuminance linearized volume obtained with full symmetry.

The set of curves 45 and 42 are representative of a close spacing of line-pair light sources. The distance between the lamps for this data set is 20 inches. Curve 45 is the light intensity variation with distance from the top mounted lamps. Curve 42 is the light intensity variation with distance from the bottom mounted lamps. The crossover point for these two curves, the point of equal light intensity from each lamp, is at 10", at the line-pair midpoint. The 20 inch lamp-to-lamp separation resulted in the highest center point light intensity, 2302 foot-candies.

The curve 42' within the set of curves 45 and 42 is the linearized total illuminance available for inspection. The high rate of change of illumination that resulted from the close spacing to the lamp limited the distance in which control of light intensity variation can be achieved. For light intensity maintenance within a limit of 10%, an excursion of ±3 inches from the equi-intensity crossover point is determined. The test volume within 10 percent light intensity variation, is 15 inches long by 12 inches deep by 6.0 inches high.

Readjustment to a lower inspection illuminance intensity range for an inspection booth is accomplished by using a single lamp in each fixture and increasing the lamp-lamp separation to 26 inches. The result of this change is a centerpoint illumination of 735 foot-candles for the same 6 inch high test volume. The shape of the summed inspection point light curve is similar to that obtained with the line-pair of point sources in FIG. 2.

The set of curves 45 and 43 are representative of a practical balance between available light intensity and a linearized light intensity volume. The distance between the lamps for this data set is 40 inches. Curve 45 is again the top lamp at a fixed position and is the light intensity variation with distance from the top mounted light source. Curve 43 is the light intensity variation with distance from the bottom light source spaced 40" from the top lamp surfaces. These curves, as in the 20" separation data set, represent the light intensity with distance from a line-pair of light sources. The minimum total light from the two sources is at the 20" midpoint between them where the light intensity from each lamp is equal. The total illumination at the centerpoint is 706 foot-candles, markedly lower than with the 20" separation, and is a good illuminance level for the inspection of injectable drugs.

The reduction of the light intensity at the center point between curves 45 and 43 is accompanied by a distinctly flatter rate of change of light intensity with distance from the mid-point. The reduced rate of change of the light intensity versus distance results in an increased distance from the mid-point in which light intensity variation is controlled. Curve 43' within the set of curve 45 and 43, is the linearized total illuminance available for inspection. The inspection volume for a maximum 10% light intensity variation has increased to a volume 15 inches long by 12 inches deep by 9.0 inches high. This volume is adequate for particle inspection of the entire range of Small Volume Injectable preparations.

The pair of curves 45 and 44 represents a tripling of the distance between the line-pair of light sources compared to the 20" spacing. The change of intensity with distance from the lamp is flatter for these curves than for either of the others. The two effects that can be seen from the increased distance between the lamps are:

1) lower centerpoint light intensity
2) an increased distance from the centerpoint in which the light intensity variation is controlled within 10%.

The 60 inch lamp-to-lamp separation produced the lowest center point light intensity, 352 foot-candles as shown in the Light Sum curve 44'. As before, the set of curves 45 and 44 is the data for the change of illuminance with distance from the surface of the top lamp. Curve 44' is the linearized total illuminance available for inspection within 10% light intensity variation. Curve 44' shows that an excursion of ±5.7 inches from the center point lies within a 10% light intensity variation. The linearized inspection volume for the 60 inch lamp to lamp spacing is therefore 15 inches long by 12 inches deep by 11.4 inches high.

To provide adequate light intensity for the critical inspection use just described, the number of lamps in each fixture is doubled to four. The result is a center point light intensity level of 704 foot candles which is maintained within 10% throughout the 15 inches long by 12 inches deep by 11.4 inches high inspection volume.

In accordance with a preferred embodiment of the present invention, the inspection station further comprises means for quickly and reversibly changing the background behind the inspection volume being utilized from light to dark in order to obviate the need for separate inspection volumes and movement.

The inspected containers of injectable products are all small enough to be conveniently held in one hand. This capability provides an alternative to moving the container to change the contrast of the particle/background combination. Using the inspector's free hand or a foot, a change of background from white to black can be initiated with either manual or mechanized means. A particular means to achieve this end is depicted in FIG. 6 and comprises an 12 inch high by 18 inch wide section 200 of 12 inch high vertical elements 201 that have an equilateral triangle cross section. The vertical elements 201 have one white surface 202 and black on the other two 203a and 203b. Flex closure elements 205 provide a continuous background with each change. The inspection commences with each of the vertical elements 201 showing a white face 202 to the observer. A solenoid driven cam 204 provides the movement required to transform the white background chosen for the detection of dark or black particles to a black background for the detection of white or light colored particles in approximately 200 milliseconds.

It is understood that other fast change physical arrangements can be used to provide a changeable background to eliminate the time and energy presently lost by an inspector in the examination for contaminating particles in injectable solutions.

The use of a switched black and white background improves the results of particle contamination inspections with either unassisted vision or with a magnifying glass. The improvement that can be obtained is however much greater when a magnifying glass is employed since maintenance of an optimum head and container position with respect to the magnifying lens is less difficult than that required for repositioning and re-optimization. The use of the switched background results in higher inspection rates and improved maintenance of selected product quality standards.

It is understood that the above discussion, drawings and specific examples are illustrative of the present invention and that changes may be made in structure, components, relative relationships, method steps and the like without departing from the scope of the present invention as defined in the following claims. Thus, method and inspection station may have similar utility with optical machine based inspection systems and with respect to machine vision magnification systems in place of optical lenses.

What is claimed is:

1. A method for enhancing the reliability of an illuminated inspection of defects in three dimensional items in an inspection station wherein the inspection station comprises an illumination source positioned on one side of an inspection volume in which a three dimensional item is positioned, and which inspection volume is visually aligned with an inspector for inspection with illumination from the illumination source; said method comprising the steps of:

a) providing a second illumination source on a second side of the inspection volume substantially directly opposite that of the first illumination source and substantially in line therewith;

b) substantially visually aligning the inspection volume with an illumination midpoint between the illumination source positioned on one side of the inspection volume and the second illumination source positioned on the side substantially opposite to the first illumination source relative to the inspection volume; and c) directly illuminating the three dimensional object with the respective illumination sources only with light therefrom which is in a substantially direct line between the respective illumination sources.

2. The method of claim 1, wherein additional illumination sources are positioned around the illumination midpoint with illumination symmetry.

3. The method of claim 1, wherein the inspection is visually conducted by a human.

4. The method of claim 1 wherein the inspection is conducted with the optical input of a machine vision system.

5. The method of claim 1, wherein the three dimensional item is a transparent vial containing an injectable solution and wherein the inspection station is provided with a changeable background behind the inspection volume relative to the inspector, wherein the background is changed from dark to light and light to dark for selective illuminated inspection of dark and light particles which may be contained in said injectable solution without moving the vial from the inspection volume.

6. The method of claim 5, wherein the inspection volume includes a volume to contain movement of the vial to place particles, which may be contained therein, into motion.

7. The method of claim 1, wherein the distance between the respective light sources is at least 20 inches and wherein illumination intensity from both light sources at the inspection volume is at least 250 foot-candles.

8. The method of claim 1, wherein both light sources are of substantially equal intensity and wherein the inspection volume is located substantially at the physical midpoint between the respective light sources.

9. The method of claim 1 wherein the three dimensional object is positioned within the inspection volume wherein light from the light sources which illuminates the inspection volume does not vary by more than 10%.

10. An inspection station for illuminated inspection of three dimensional items for defects therein, with enhanced reliability, wherein the inspection station comprises an illumination source positioned on one side of an inspection volume in which a three dimensional item is positioned, and which inspection volume is visually aligned with an inspector for human inspection with illumination from the illumination source; characterized in that the inspection station further comprises a second illumination source on a second side of the inspection volume substantially directly opposite that of the first illumination source and substantially in line therewith; wherein the inspection volume is substantially aligned with an illumination midpoint between the illumination source positioned on one side of the inspection volume and the second illumination source positioned on the side substantially opposite to the first illumination source relative to the inspection volume; whereby there is direct illumination of the three dimensional object by the respective illumination sources only with light therefrom which is in a substantially direct line between the respective illumination sources.

11. The inspection station of claim 10, wherein additional illumination sources are positioned around the illumination midpoint with illumination symmetry.

12. The inspection station of claim 10, wherein the three dimensional item is a transparent vial containing an injectable solution and wherein the inspection station comprises means for selectively changing the background behind the inspection volume relative to the inspector, from dark to light and light to dark for selective illuminated inspection of dark and light particles which may be contained in said injectable solution, without moving the vial from the inspection volume.

13. The inspection station of claim 12, wherein the inspection volume includes a volume to contain movement of the vial to place particles, which may be contained therein, into motion.

14. The inspection station of claim 10, wherein the distance between the respective light sources is at least 20 inches and wherein illumination intensity from both light sources at the inspection volume is at least 250 foot-candles.

15. The inspection station of claim 10, wherein both light sources are of substantially equal intensity and wherein the inspection volume is located substantially at the physical midpoint between the respective light sources.

16. The inspection station of claim 10, wherein a magnifying lens is interposed between the inspector and the inspection volume.

17. The inspection station of claim 10, wherein a machine vision magnification system is interposed between the inspector and the inspection volume.

18. An inspection station for illuminated inspection of three dimensional items, for defects therein, with enhanced reliability, wherein the inspection station comprises an illumination source positioned on one side of an inspection volume in which a three dimensional item is positioned, and which inspection volume is visually aligned with any one of automated and manual inspection means for inspection with illumination from the illumination source; characterized in that the inspection station further comprises a second illumination source on a second side of the inspection volume substantially directly opposite that of the first illumination source and substantially in line therewith; wherein the inspection volume is substantially aligned with an illumination midpoint between the illumination source positioned on one side of the inspection volume and the second illumination source positioned on the side substantially opposite to the first illumination source relative to the inspection volume whereby the three dimensional object is illuminated with the respective illumination sources only with light therefrom which is in a substantially direct line between the respective illumination sources.

19. The method of claim 18, wherein additional illumination sources are positioned around the illumination midpoint with illumination symmetry.

20. The inspection station of claim 18, wherein the inspection volume is sized such that light from the light sources does not deviate within the inspection volume by more than 10%.

* * * * *